United States Patent
Tsukii et al.

(10) Patent No.: US 9,541,489 B2
(45) Date of Patent: Jan. 10, 2017

(54) OPTICAL MEASURING APPARATUS AND SPECIMEN DISCRIMINATING AND DISPENSING APPARATUS

(75) Inventors: Ken Tsukii, Tokyo (JP); Toru Takahashi, Tokyo (JP); Jie Xu, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 544 days.

(21) Appl. No.: 13/176,781

(22) Filed: Jul. 6, 2011

(65) Prior Publication Data

US 2012/0004864 A1 Jan. 5, 2012

Related U.S. Application Data

(63) Continuation of application No. PCT/JP2009/050014, filed on Jan. 6, 2009.

(51) Int. Cl.
*G01F 7/00* (2006.01)
*G01N 15/14* (2006.01)
(Continued)

(52) U.S. Cl.
CPC .......... *G01N 15/14* (2013.01); *G01F 1/7086* (2013.01); *G01F 15/07* (2013.01); *G01N 2015/149* (2013.01)

(58) Field of Classification Search
CPC ........ G01F 1/7086; G01F 15/07; G01F 15/14; G01F 2015/149
(Continued)

(56) References Cited

U.S. PATENT DOCUMENTS 5,170,438 A * 12/1992 Anger .................... G01F 1/704
382/100
5,679,575 A * 10/1997 Kubota et al. ............... 436/49
(Continued)

FOREIGN PATENT DOCUMENTS

CN 1973195 A 5/2007
JP 56-154667 11/1981
(Continued)

OTHER PUBLICATIONS

International Search Report issued on Feb. 3, 2009 in corresponding International Application No. PCT/JP2009/050014.
(Continued)

*Primary Examiner* — John Breene
*Assistant Examiner* — Stephanie Bloss
(74) *Attorney, Agent, or Firm* — Oblon, McClelland, Maier & Neustadt, L.L.P.

(57) ABSTRACT

The invention provides an optical measuring apparatus having a plurality of measuring sections each having a light irradiating section for irradiating light to specimens and a light receiving section for receiving optical data acquired by irradiating the light to the specimens and a flow rate calculating section for calculating flow rate values of the specimens based on a difference of measured times of the optical data measured by the plurality of measuring sections with respect to the specimens and a distance between the plurality of measuring sections. The optical measuring apparatus measures the optical data of the specimens by irradiating light to the specimens, i.e., the objects to be measured, dispersed within a sample fluid flowing through a flow passage. The optical measuring apparatus further includes a flow rate graph generating section for generating flow rate graph data in which the values of flow rate of the specimens calculated by the flow rate calculating section are arrayed in (Continued)

order of calculation in time-series manner and for outputting the generated flow rate graph data to a displaying section.

10 Claims, 4 Drawing Sheets

(51) Int. Cl.
  *G01F 1/708* (2006.01)
  *G01F 15/07* (2006.01)
(58) Field of Classification Search
  USPC .......................................................... 702/49
  See application file for complete search history.

(56) References Cited

U.S. PATENT DOCUMENTS

| 7,957,002 B2 | 6/2011 | Tsukii et al. | |
|---|---|---|---|
| 2008/0000307 A1* | 1/2008 | Gysling | G01F 1/708 73/861.44 |
| 2008/0231860 A1* | 9/2008 | Melnyk | G01F 1/712 356/484 |
| 2008/0257072 A1* | 10/2008 | Takahashi | B01F 5/0057 73/864.11 |
| 2010/0233753 A1 | 9/2010 | Tsukii et al. | |
| 2011/0199612 A1 | 8/2011 | Tsukii et al. | |

FOREIGN PATENT DOCUMENTS

| JP | 2000-205905 | 7/2000 |
|---|---|---|
| JP | 2001-99848 | 4/2001 |
| JP | 2007-64759 | 3/2007 |
| JP | 2007-97411 A | 4/2007 |
| JP | 2007-121179 A | 5/2007 |
| JP | 2008-116381 A | 5/2008 |
| JP | 2009-2710 A | 1/2009 |
| WO | WO 2005/103642 A1 | 11/2005 |

OTHER PUBLICATIONS

Tatsuro Yamashita et al., "Basic Theory of FACS (2), Fundamental Theorem and Basic Operations for Sorting", Cell Technology, vol. 16, No. 10, 1997, pp. 1532-1541.
Japanese Office Action issued May 14, 2012, in Patent Application No. 2007-161927 (with English-language translation).
U.S. Appl. No. 12/403,701, filed Mar. 13, 2009, Tsukii, et al.
Office Action issued Dec. 26, 2011, in Japanese Patent Application No. 2007-161927 (with English-language translation).
Combined Chinese Office Action and Search Report issued Sep. 21, 2012 in Chinese Patent Application No. 200980153167.9 (with English-language translation).

* cited by examiner

OPTICAL MEASURING APPARATUS AND SPECIMEN DISCRIMINATING AND DISPENSING APPARATUS

FIELD OF THE INVENTION

The present invention relates to an optical measuring apparatus and a specimen discriminating and dispensing apparatus. More specifically, the invention relates to an optical measuring apparatus and a specimen discriminating and dispensing apparatus capable of improving measurement reliability of optical data of specimens by flowing the specimens dispersed within a sample fluid flowing through a flow passage methodically while perceiving an actual flow condition and by sorting the specimens by values of their flow rates.

BACKGROUND ART

There is proposed a method of setting a fluid flow so that a fluid containing specimens (minute objects to be tested) such as cells dispersed therein flows within a capillary tube, of measuring optical data (fluorescent data) of the specimens within the fluid flow by irradiating light from a light source to the fluid flow and of discriminating the specimens by the measured optical data. Ultrasonic vibrations are applied to the fluid in a dispensing section to form droplets after discriminating the specimens and an electric charge of several hundred volts for example is applied to the droplets. Then, a voltage of several thousand volts is applied to the charged droplets from a deflecting plate, so that the droplets are dispensed to arbitrary containers (wells) of the dispensing section while dividing positions to which the respective droplets drop into plus and minus electrode-sides.

[Non-Patent Document 1] Tatsuro Yamashita, Shinichiro Niwa, "Cell Technology" Vol. 16, No. 10, p 1532-1541, 1997

DISCLOSURE OF THE INVENTION

Problems to be Solved by the Invention

In the case of flowing the fluid (sample fluid) in which the specimens are dispersed within the pipe line as described above, the sample fluid is flown at a center part of the pipe line by making the flow of sample fluid (sample flow) so that it is surrounded by a flow of sheath fluid (sheath flow) by utilizing a sheath flow technology. At this time, pressures of the sample and sheath flows are controlled by pressures regulated by regulators and position within a cross-section of the pipe line where the specimen flows and a flow rate of the sample flow are regulated to be conditionally constant. Still more, measured parameters detected by pressure sensors of the sample and sheath flows are fed back to control the pressures of the sample and sheath flows by adjusting the pressures regulated by the regulators and to regulate the flow rate of the sample flow to be conditionally constant (feedback control).

However, because the prior art method determines the regulated pressures from flow volumes and measured parameters of the sample and sheath flows, conditions in which the specimens flow within the pipe line (flow condition) can be judged only from the measurement parameters. Due to that, there is a problem that it is unable to perceive an actual flow condition within the pipe line. For instance, there is a problem that the flow rate varies even if the pressure is conditionally set to be equal when clogging or adhesion of foreign matters occurs within the pipe line.

Accordingly, the present invention aims at solving the aforementioned problem by providing an optical measuring apparatus and a specimen discriminating and dispensing apparatus capable of improving measurement reliability of optical data of specimens by flowing the specimens dispersed within a sample fluid through a flow passage methodically while perceiving an actual flow condition and by sorting the specimens by values of flow rate.

Means for Solving the Problems

There is provided the following invention to solve the prior art problem described above.

According to a first aspect of an optical measuring apparatus of the invention, the optical measuring apparatus measures optical data of specimens, i.e., objects to be measured, dispersed in a sample fluid flowing within a flow passage by irradiating light to the specimens. The optical measuring apparatus includes a plurality of measuring sections each having a light irradiating section for irradiating light to the specimens and a light receiving section for receiving optical data acquired by irradiating the light to the specimens and a flow rate calculating section for calculating values of flow rate of the specimens based on a difference of measured times of the optical data measured by the plurality of measuring sections with respect to the specimens and a distance between the plurality of measuring sections.

According to a second aspect of the optical measuring apparatus of the invention, the values of flow rate of the specimens calculated by the flow rate calculating section are adopted as measurement parameters for judging flow conditions of the sample fluid.

According to a third aspect of the optical measuring apparatus of the invention, the optical measuring apparatus further includes a flow rate graph generating section for generating flow rate graph data in which the values of flow rate of the specimens calculated by the flow rate calculating section are arrayed in order of calculation in a time-series manner and outputting the generated flow rate graph data to a display section.

According to a fourth aspect of the optical measuring apparatus of the invention, the optical measuring apparatus further includes a flow condition judging section for judging the flow condition of the specimens within the flow passage based on the measurement parameters including the values of flow rate of the specimens and outputting the judged resultant data to an output section including the display section.

According to a fifth aspect of the optical measuring apparatus of the invention, the flow rate graph generating section includes an area range specifying section for specifying a desired graph area range within the entire flow rate graph data and acquiring the values of flow rate of the specimens within the specified graph area range, generates flow rate graph data in which the values of flow rate of the specimens acquired by the area specifying section are arrayed in a time-series manner in order calculated by the flow rate calculating section and outputs the generated flow rate graph data to the display section.

According to a first aspect of a specimen discriminating and dispensing apparatus of the invention, the specimen discriminating and dispensing apparatus for sorting object specimens, i.e., objects to be sorted, among specimens, i.e., objects to be measured, dispersed in a sample fluid flowing through a flow passage, comprising: the optical measuring apparatus described in any one of claims 1 through 5; and a dispensing section for dispensing the specimens discriminated based on the measurement parameters measured by the optical measuring apparatus to dispensing object regions through a nozzle.

According to a second aspect of the specimen discriminating and dispensing apparatus of the invention, the specimen discriminating and dispensing apparatus sorts the specimens corresponding to the flow rate graph data within the graph area range specified by the area specifying section of the optical measuring apparatus as the object specimens.

According to a third aspect of the specimen discriminating and dispensing apparatus of the invention, the specimen discriminating and dispensing apparatus dispenses the object specimen from the tip of the nozzle to the dispensing object region even if the flow rate of the measured object specimen varies in sorting the specimens corresponding to the flow rate graph data within the graph area range specified by the area specifying section of the optical measuring apparatus by calculating a time for dispensing the object specimen based on a relationship related to the measured flow rate of the object specimen.

According to a fourth aspect of the specimen discriminating and dispensing apparatus of the invention, the specimen discriminating and dispensing apparatus dispenses one or a plurality of measured objects to the dispensing object regions after going through a flow rate slower than a flow rate at position where the specimen, i.e., the object to be measured, is measured.

According to a fifth aspect of the specimen discriminating and dispensing apparatus of the invention, the specimen discriminating and dispensing apparatus dispenses the objects to be measured, i.e., the specimen, to the dispensing object region by switching a positional relationship between the tip of the nozzle of the pipe line and the dispensing object region by a time for dispensing the object to be measured calculated based on the measured and calculated flow rate.

Advantageous Effects of the Invention

The optical measuring apparatus and specimen discriminating and dispensing apparatus of the invention allow the users to perceive the actual flow condition by adopting the flow rate of each specimen flowing through the flow passage as the measurement parameter. That is, it becomes possible for the users to confirm whether or not the pipe line is causing an abnormality such as clogging and adhesion of foreign materials. For instance, the optical measuring apparatus and the specimen discriminating and dispensing apparatus allow the users to perceive the flow condition by displaying the graphs in which the flow rate of each specimen with respect to measured time is presented in time-series manner and by displaying the other measurement parameters. They also allow the user to perceive an abnormality in a short time, when the abnormality occurs, by displaying the abnormal state on the display or by outputting a sound and permits to shorten the time for recovering to the normal state.

It is also possible to measure invariable optical data by stabilizing the flow rate by letting the users perceive the flow condition and to thus accurately execute the dispensing operation.

Still more, it becomes possible to suppress variation of the dispensed objects by selecting and dispensing the specimen whose flow rate is invariable because irradiation density of light varies depending on locations within the flow passage. It is also possible to measure invariable optical data by measuring the optical data again. Thus, it becomes possible to execute the dispensing operation accurately and efficiently.

DESCRIPTION OF REFERENCE NUMERALS

10 Optical Measuring Apparatus
11a, 11b Measuring Section
12 Flow Rate Calculating Section
13 Flow Rate Graph Generating Section
14 Flow Condition Judging Section
15 Display Section
70 Nozzle
80 Dispensing Section
300 Area Specifying Section
1000 Specimen Discriminating and Dispensing Apparatus
S Specimen (Sample)
W Well

BEST MODE FOR CARRYING OUT THE INVENTION

One embodiment of the invention will be explained below with reference to the drawings. It is noted that the embodiment described below is described for the purpose of only explanation and does not limit a scope of the invention by any means. Accordingly, although a person skilled in the art may adopt an embodiment by replacing each or all components of the embodiment of the invention with same or corresponding components, such embodiment shall be also included within the scope of the invention.

Figure 1:
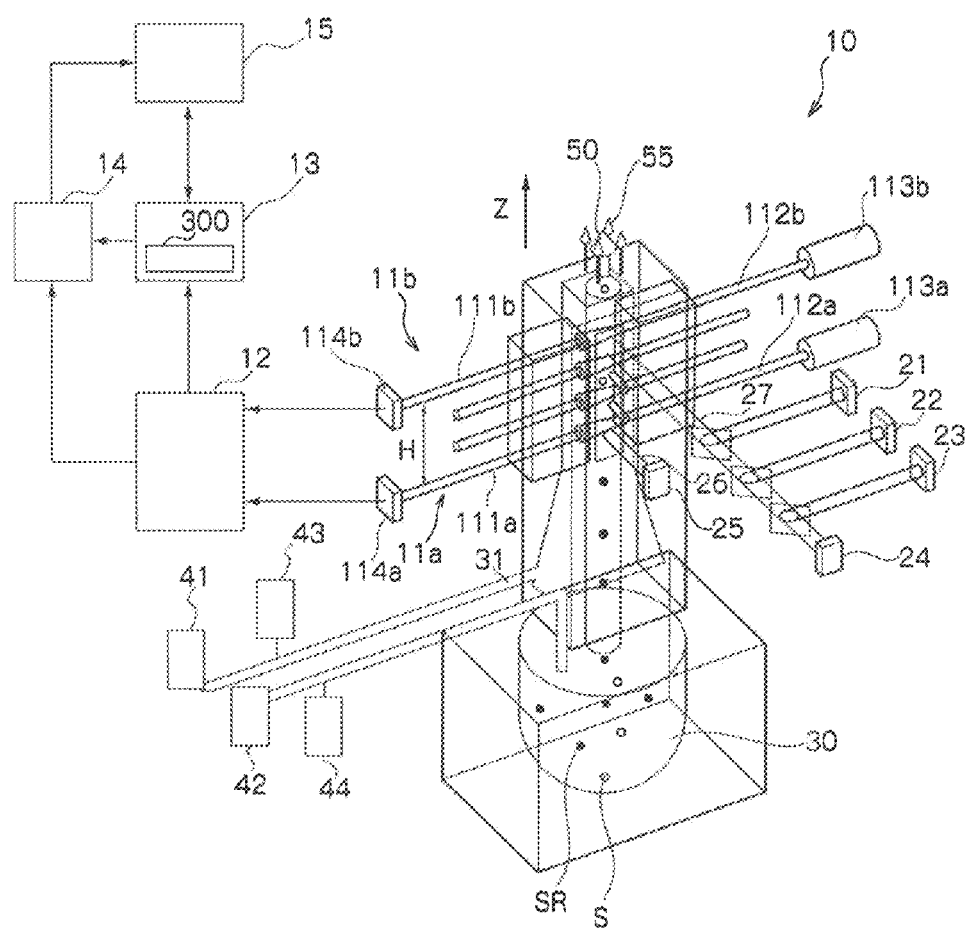
FIG. 1 is a perspective view of a preferred embodiment of an optical measuring apparatus of the invention.

FIG. 1 is a perspective view of a preferred embodiment of an optical measuring apparatus of the invention.

As shown in FIG. 1, the optical measuring apparatus 10 has two measuring sections 11a and 11b for measuring optical data of transmitted light irradiated to specimens, a flow rate calculating section 12 for calculating flow rates of the specimens, a flow rate graph generating section 13 for generating flow rate graph data and a flow condition judging section 14 for judging flow conditions.

A plurality of specimens S and SR will be referred to also as micro-objects to be detected or as samples and are dispersed within a sample fluid 30 in the present embodiment. A flow of the sample fluid 30 will be referred to as a sample fluid 50 and flows of sheath fluid 31 that surround the sample flow 50 will be referred to as sheath flows 55. Here, the specimens S are assumed to be object specimens to be dispensed and the specimens SR to be non-object specimens to be disposed here.

The measuring section 11a is provided with a laser (light source) 113a, an irradiating optical fiber 112a, a transmitted light receiving fiber 111a and a light receiving element (PD) 114a. The measuring section 11b is also provided with a laser 113b, an irradiating optical fiber 112b, a transmitted light receiving fiber 111b and a light receiving element (PD) 114b.

The measuring section 11a irradiates exciting light irradiated from the laser 113a to the specimens S and SR passing through the sample flow 50 through the irradiation optical fiber 112a and receives transmitted light by the PD 114a through the light receiving fiber 111a that receives the transmitted light. Then, the measuring section 11a transmits data on measured time when the light is received by the PD 114a to the flow rate calculating section 12.

In the same manner with the measuring section 11a, the measuring section 11b distant from the measuring section 11a by a predetermined distance H in a flow passage direction (Z-direction) also receives transmitted light irradiated to the specimens S and SR passing through the sample flow 50 and transmits data on measured time when the light is received to the flow rate calculating section 12.

Accordingly, two measured time data measured at the measuring sections 11a and 11b with respect to the same specimens S and SR are transmitted to the flow rate calculating section 12. It is noted that although the predetermined distance H is not specifically limited, it is about 750 μm which is equal to a size of diameters of three optical fibers in the embodiment of FIG. 1.

A regulator 42 controls and regulates pressure of the sample flow 50 and a pressure sensor 44 measures the pressure. The pressure measured by the pressure sensor 44 is used as a measurement parameter to judge the flow condition or is used for feedback control of the pressure of the sample flow 50.

A regulator 41 also controls and regulates pressure of the sheath flow 55 and a pressure sensor 43 measures the pressure. The pressure measured by the pressure sensor 43 is used as a measurement parameter to judge the flow condition or is used for feedback control of the pressure of the sheath flow 55.

The measuring section 11a in FIG. 1 also receives fluorescent data of the specimens S and SR through a side light receiving fiber 26 and side scattered light data through a photomultiplier (PMT) 25. Still more, the measuring section 11b receives fluorescent data of the specimens S and SR through a side light receiving fiber 27 and side scattered light data through a photomultipliers 21, 22, 23 and 24. The optical data received by the PMTs 21, 22, 23, 24 and 25 is used to discriminate the specimens S and SR.

The flow rate calculating section 12 in FIG. 1 calculates values of flow rate of the specimens S and SR based on the two measured time data measured by the measuring sections 11a and 11b with respect to the same specimens S and SR and on the distance H between the measuring sections 11a and 11b.

The flow rate graph generating section 13 in FIG. 1 generates flow rate graph data in which the values of flow rate of the specimens S and SR calculated by the flow rate calculating section 12 are arrayed in order of calculated time and outputs the generated flow rate graph data to the displaying section 15 to display the flow rate graph.

Figure 2:
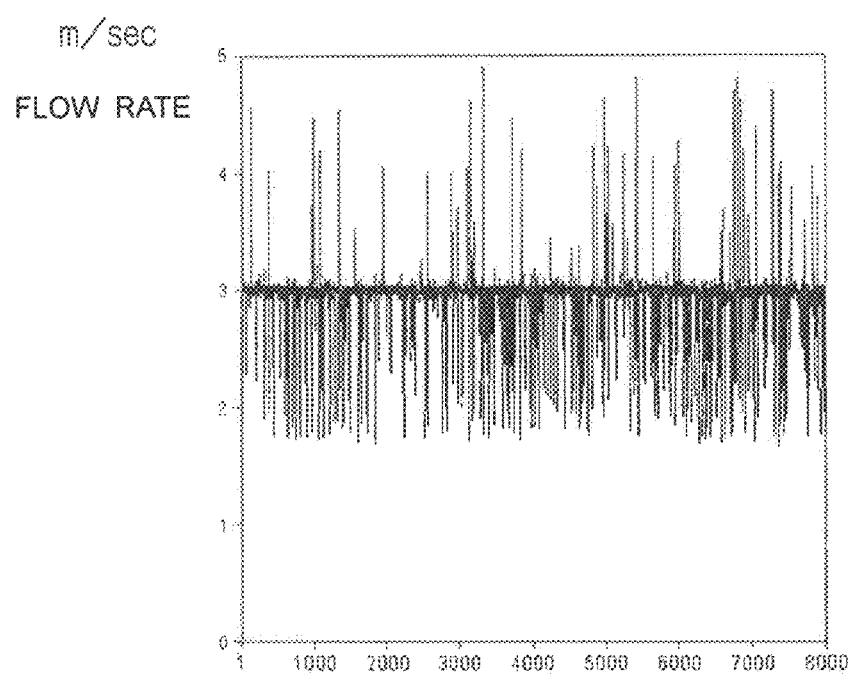
FIG. 2 is a graph showing one exemplary flow rate graph.

FIG. 2 shows one exemplary flow rate graph. FIG. 2 denotes the flow rate along an axis of ordinate and the specimens S and SR sequentially along an axis of abscissas. The displaying section 15 displays FIG. 2 so that users can perceive the flow rate conditions of the specimens S and SR within the sample flow 50.

The flow rate graph generating section 13 also has an area specifying section 300 that allows the users to specify a desired graph area range within the flow rate graph displayed on the displaying section 15 through an input section not shown and that acquires the values of flow rate within the specified graph area range. Then, the flow rate graph generating section 13 generates flow rate graph data in which the values of flow rate of the specified area range are arrayed again in order of calculated time and outputs the generated flow rate graph data to the displaying section 15 to display the flow rate graph.

Figure 3:
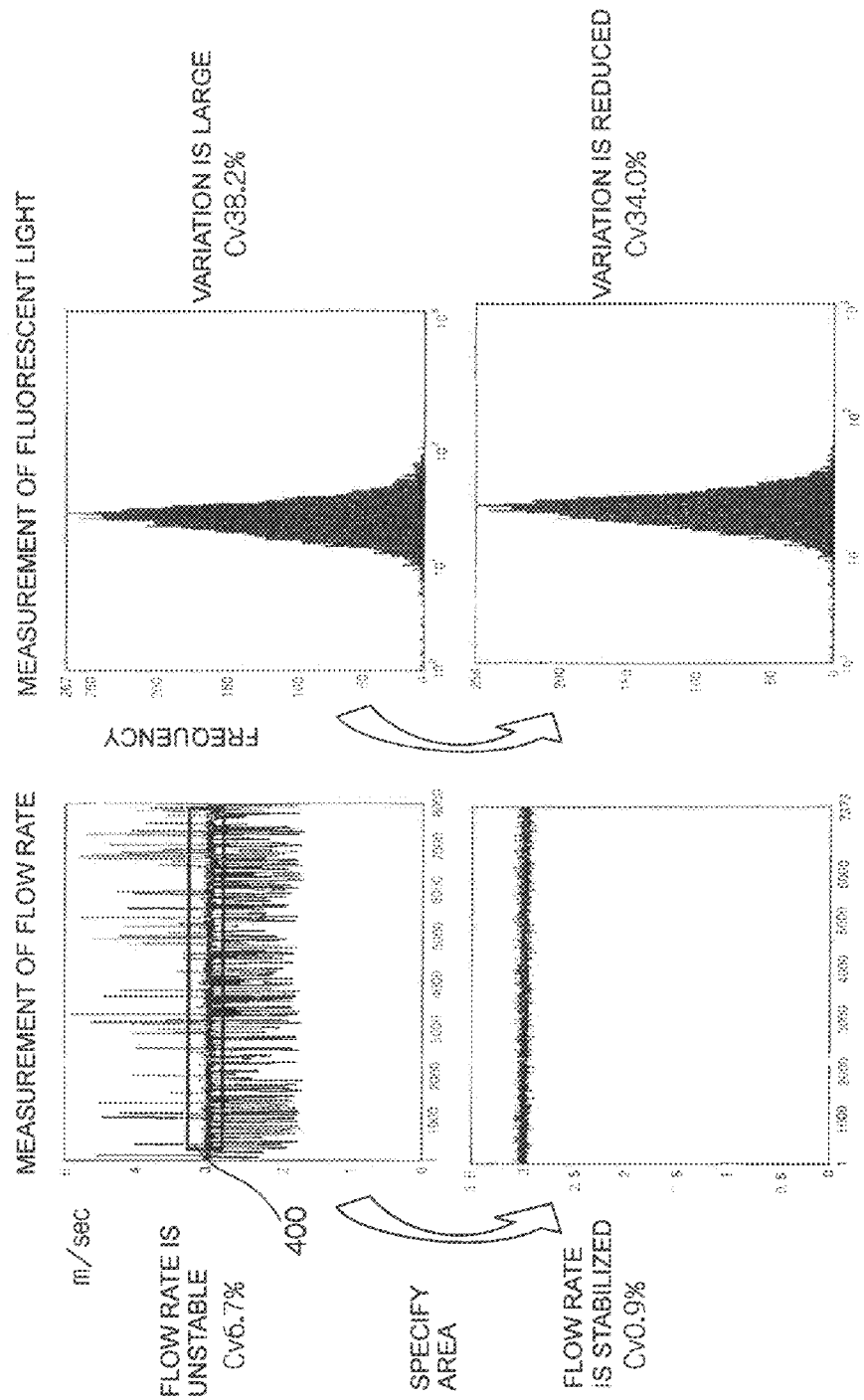
FIGS. 3a and 3b are graphs showing one exemplary specified area range of the flow rate graph data.

FIGS. 3a and 3b are graphs showing one exemplary specified area range of the flow rate graph data, wherein FIG. 3a shows a measurement result of the flow rate and FIG. 3b shows a measurement result of fluorescent light. As shown in FIG. 3a, as a result of specifying a graph area range 400 within the flow rate graph shown in FIG. 2, the specimens within the specified range present a flow rate graph in which the values of flow rate are stable. That is, a coefficient of variation Cv of the flow rate drops from 6.7% to 0.9%. Still more, a coefficient of variation Cv of frequency of peaks of the fluorescent data measured from the specimens within the specified range drops from 38.2% to 34.0%. Thus, the variations drop as a result.

The flow condition judging section 14 in FIG. 1 judges the flow condition by analyzing the various parameters such as the flow rate graph data generated by the flow rate graph generating section 13 and the measured parameters such as the values of flow rate calculated by the flow rate calculating section 12, the pressure of the sample flow 50 and the sheath flow 55 measured by the pressure sensors 43 and 44 and others and outputs the flow condition to the displaying section 15 to enable the users to perceive the flow condition.

Thus, the optical measuring apparatus 10 of the embodiment of the invention described above allows the users to perceive the actual flow condition by calculating the flow rates of the specimens S and SR and by setting the calculated flow rates as the measurement parameters. For instance, the optical measuring apparatus 10 allows the users to perceive the flow condition by displaying the flow rate of each specimen as the graph in a time-series manner with respect to the measured time and the other measurement parameters on the display. When an abnormality occurs, the optical measuring apparatus 10 also allows the users to perceive the abnormality by displaying the abnormal state on the display and by outputting a sound and permits to shorten a time for recovering to a normal state.

Figure 4:
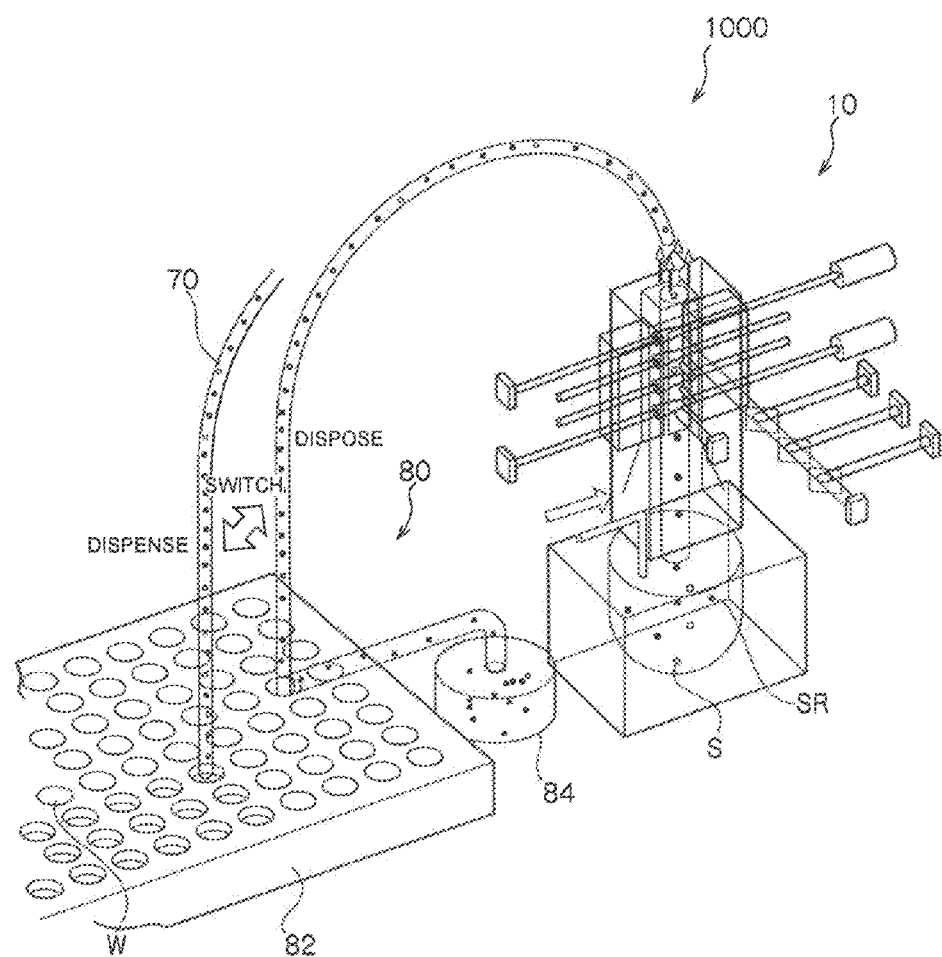
FIG. 4 is a perspective view of a preferred embodiment of a specimen discriminating and dispensing apparatus of the invention using the optical measuring apparatus.

Next, one exemplary specimen discriminating and dispensing apparatus using the optical measuring apparatus 10 will be explained. FIG. 4 is a perspective view of a preferred embodiment of the specimen discriminating and dispensing apparatus of the invention using the optical measuring apparatus 10.

As shown in FIG. 4, the specimen discriminating and dispensing apparatus 1000 has the optical measuring apparatus 10 and a specimen dispensing section 80. As described above, the optical measuring apparatus 10 discriminates the specimens S and SR by measuring the optical data of the specimens S and SR and judges the flow condition by calculating the values of flow rate of the specimens S and SR.

The dispensing section 80 injects the plurality of specimens S discriminated by the optical measuring apparatus 10 to wells (one exemplary container) W located at an arbitrary dispensing object region of a culture plate 82 (referred to simply as a plate hereinafter) through a nozzle 70 or disposes the specimens SR to be disposed to a waste fluid tank 84 through the nozzle 70. Here, the plate 82 has a plurality of wells W which are arrayed in matrix with a certain pitch along X-axis and Y-axis directions. A distance of the pitch depends on a shape of a tip of the nozzle 70 and may be what prevents the sample fluid overflowing from the well W from entering the neighboring well W. That is, the pitch distance may be narrow if the well W is deep and if the well W is shallow, the pitch distance is widened as much as possible. It is noted that the tip of the nozzle 70 can be readily inserted into the well W if a diameter of the well W is about two times of an outer diameter of the tip of the nozzle 70.

The specimen discriminating and dispensing apparatus 1000 executes the dispensing process by calculating a time (arrival time) when the specimens S and SR arrive to the tip of the nozzle 70 based on the values of flow rate calculated by the optical measuring apparatus 10 and by controlling the operations of the dispensing section 80 and the nozzle 70 based on the calculated arrival time.

Thereby, the specimen discriminating and dispensing apparatus 1000 can measure the invariable optical data and can execute the dispensing operation accurately by stabilizing the flow rates by allowing the users to perceive the flow condition.

Still more, it is possible to measure invariable optical data by dispensing the specimens S and SR which are selected by the area specifying section 300 of the optical measuring apparatus 10 and whose flow rates are stable and by measuring the optical data by the optical measuring apparatus 10 again. Thus, it becomes possible to execute the dispensing operation accurately and efficiently.

By the way, the present invention is not limited to the embodiment described above and may be modified variously.

For instance, it becomes possible to let the users to perceive an abnormality quickly by adding a sound output section, a lamp and others to the apparatus shown in FIG. 1 when the abnormality is found in the flow condition. Still more, it becomes possible to let the users to execute operations for recovering from the abnormal state.

Furthermore, it is possible to avoid a serious abnormality from occurring by allowing the users to perceive the flow condition.

Although the dispensing section 80 is the plate in the embodiment described above, it is not limited to be a plate and may be a tube, dish and the like.

The exciting light of the invention may be also referred to as a measuring light or an irradiation light.

The optical measuring apparatus of the invention is applicable to all kinds of fields requiring inspection, observation and analysis related to biological polymers such as genes, immune systems, proteins, amino acids and sugar groups, e.g., to fields of engineering, agriculture in general such as food, agriculture and seafood processing, pharmacy, medicines such as sanitary, health, immune, diseases and genetics and sciences such as chemistry and biology.

The invention claimed is:

1. An optical measuring apparatus for measuring optical data of specimens, which are objects to be measured, dispersed in a sample fluid flowing within a flow passage by irradiating light to said specimens, comprising:
   a plurality of measuring sections each having a light irradiating section for irradiating light to said specimens and a light receiving section for receiving the optical data acquired by irradiating the light to said specimens;
   a flow rate calculating section implemented by circuitry, the circuitry configured to calculate values of flow rate of said specimens based on a difference of measured times of said optical data measured by said plurality of measuring sections with respect to said specimens and a distance between said plurality of measuring sections; and
   a flow rate graph generating section implemented by the circuitry, the circuitry configured to generate flow rate graph data in which the values of flow rate of said specimens calculated by said flow rate calculating section are arrayed in order of calculation in a time-series manner and outputting said generated flow rate graph data to a display section to display a flow rate graph,
   wherein said flow rate graph generating section includes an area range specifying section implemented by the circuitry, the circuitry configured to specify a desired graph area range within said entire flow rate graph data of said previously generated flow rate graph, acquire the plurality of values of flow rate of said specimens only within said specified graph area range of flow rate, and exclude unnecessary values of flow rate outside of said specified graph area range of flow rate to drop a variation of the frequency of optical data of specimens.

2. The optical measuring apparatus according to claim 1, wherein the values of flow rate of said specimens calculated by said flow rate calculating section are adopted as measurement parameters for judging flow conditions of said sample fluid.

3. The optical measuring apparatus according to claim 2, further comprising a flow condition judging section implemented by the circuitry, the circuitry configured to judge the flow condition of said specimens within said flow passage based on said measurement parameters including the values of flow rate of said specimens and outputting the judged resultant data to an output section including said display section.

4. The optical measuring apparatus according to claim 1, wherein said flow rate graph generating section generates flow rate graph data in which the values of flow rate of said specimens acquired by said area specifying section are arrayed in a time-series manner in order calculated by said flow rate calculating section; and
   outputs said generated flow rate graph data to said display section.

5. A specimen discriminating and dispensing apparatus for sorting object specimens among specimens, that are objects to be measured, dispersed in a sample fluid flowing through a flow passage, comprising:
   the optical measuring apparatus described in any one of claims 1, 2 or 3; and
   a dispensing section for dispensing said specimens discriminated based on said measurement parameters measured by said optical measuring apparatus to dispensing object regions through a nozzle.

6. The specimen discriminating and dispensing apparatus according to claim 5, wherein said specimen discriminating and dispensing apparatus sorts said specimens corresponding to said flow rate graph data within said graph area range specified by said area specifying section of said optical measuring apparatus as said object specimens.

7. The specimen discriminating and dispensing apparatus according to claim 6, wherein said specimen discriminating and dispensing apparatus dispenses the object specimens from a tip of said nozzle to said dispensing object region when the flow rate of said measured object specimen varies in sorting said specimens corresponding to said flow rate graph data within said graph area range specified by said area specifying section of said optical measuring apparatus, and
   wherein the specimen discriminating and dispensing apparatus dispenses the object specimens by calculating a time for dispensing the object specimen based on a relationship related to the measured flow rate of the object specimen.

8. The specimen discriminating and dispensing apparatus according to claim 7, wherein said specimen discriminating and dispensing apparatus dispenses one or a plurality of measured objects to said dispensing object regions after going through a flow rate slower than a flow rate at position where the specimen is measured.

9. The specimen discriminating and dispensing apparatus according to claim 8, wherein said specimen discriminating and dispensing apparatus dispenses said object to be measured to said dispensing object region by switching a positional relationship between the tip of the nozzle of a pipe line and said dispensing object region by a time for dispensing said object to be measured calculated based on the measured and calculated flow rate.

10. The optical measuring apparatus according to claim 1, wherein the plurality of values of flow rate of said specimens are acquired within said specified graph area range of flow rate independently of a calculated time period.

* * * * *